United States Patent
Burman et al.

(10) Patent No.: US 6,613,793 B2
(45) Date of Patent: Sep. 2, 2003

(54) ANTICANCER ACTIVITY OF IMINO ACID CONJUGATES OR METHYLGLYOXAL

(75) Inventors: Anand C. Burman, London (GB); Rama Mukherjee, Gurgaon Haryana (IN); Manu Jaggi, Gurgaon Haryana (IN); Anu T. Singh, Delhi (IN); Kamal K. Kapoor, Delhi (IN); Sudhanand Prasad, Delhi (IN); Manju Ray, Kolkata (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 10/187,420

(22) Filed: Jul. 1, 2002

(65) Prior Publication Data

US 2003/0118627 A1 Jun. 26, 2003

Related U.S. Application Data

(60) Provisional application No. 60/302,637, filed on Jul. 2, 2001.

(51) Int. Cl.[7] ............................................. A61K 31/40
(52) U.S. Cl. ....................................... 514/423; 548/530
(58) Field of Search ........................... 514/423; 548/530

(56) References Cited

U.S. PATENT DOCUMENTS

| 3,565,794 A | 2/1971 | Pigache | 208/326 |
| 4,066,650 A | 1/1978 | Egyud | 260/281 G |
| 5,849,783 A | * 12/1998 | Egyud | 514/425 |

FOREIGN PATENT DOCUMENTS

| EP | 0135444 | 3/1985 |
| WO | 9900362 | 1/1999 |

OTHER PUBLICATIONS

Moss, J., et al. "Prodrugs of peptides. 5. Protection ot the pyroglutamyl residue against pyroglutamyl aminopeptidase by bioreversible . . . derivatives", *Int'l J. Pharmaceutics*, vol. 52, p. 255–263, (1989).

Bundgaard, H., et al. "Prodrug derivatives of thyrotropic–releasing hormone and other peptides" *Biochemical Society Transactions*, vol. 17, p. 947–949, (1989).

Roth, E., et al. "Amidoalkylation of Aromatics with Glyoxylic Acid–γ–Lactam Adducts: 2–Pyrrolidinone, Pyroglutamic Acid . . . Ester" *Tetrahedron*, vol. 51, No. 3, p. 801–810, (1995).

* cited by examiner

*Primary Examiner*—Joseph K. McKane
*Assistant Examiner*—Rei Tsang Shiao
(74) *Attorney, Agent, or Firm*—Ladas & Parry

(57) ABSTRACT

The invention relates to the use of imino acid conjugates of methylglyoxal for the inhibition and/or treatment of cancer. The invention relates more specifically to the use imino acid conjugates of methylglyoxal for inhibition and/or treatment of cancer of the Colon, Prostate, Larynx, Kidney, Pancreas, Lung, Breast, Intestine, Oral cavity, Ovary, Glioblastoma, and Leukemia. The invention also relates to compositions and methods of inhibiting cancer using imino acid conjugates of methylglyoxal.

15 Claims, 1 Drawing Sheet

FIGURE 1

ANTICANCER ACTIVITY OF IMINO ACID CONJUGATES OR METHYLGLYOXAL

This application claims benefit of Provisional application No. 60/302,637 filed on Jul. 2, 2001.

FIELD OF THE INVENTION

The invention relates to the use of imino acid conjugates of methylglyoxal for the inhibition and/or treatment of cancer. The invention relates more specifically to the use imino acid conjugates of methylglyoxal for inhibition and/or treatment of cancer of the Colon, Prostate, Larynx, Kidney, Pancreas, Lung, Breast, Intestine, Oral cavity, Ovary, Glioblastoma, and Leukemia. The anticancer activity of the conjugates is attributed to the inhibition of the activity of glyceraldehyde 3 phosphate dehydrogenase enzyme. The invention also relates to compositions and methods of inhibiting cancer using imino acid conjugates of methyglyoxal.

BACKGROUND OF THE INVENTION

As early as 1913 it had been observed that ketoaldehydes such as, methylglyoxal could be converted to corresponding hydroxyl acids (methylglyoxal to D-lactate) by strong and ubiquitous enzyme present in various animal tissues. It was then widely held that methylglyoxal was a key intermediate of glucose breakdown. But with the elucidation of Embden-Meyerh of pathway of glycolysis, this idea was rejected. Although no definite enzyme was identified or isolated, several investigators time to time reported the formation of methylglyoxal in different organisms (Current Science 75, 103–113; 1998).

Cooper and his co-investigators established that the enzyme methylglyoxal synthase which converts the glycolytic intermediate dihydroxyacetone phosphate to methylglyoxal is present in a variety of bacteria (Annu Rev Microbiol 38, 49–68; 1984). In the early 1980s, Ray and Ray began a thorough investigation of the enzymes involved in the synthesis and breakdown of methylglyoxal in a mammalian system. Mainly by their work and also by the investigations from other laboratories, the metabolic pathway of methylglyoxal in a mammalian system had been established. In the process, they had isolated, purified and partially characterized a battery of enzymes involved. Thereafter the pathway for methylglyoxal metabolism has been elucidated in yeast, bacteria and protozoa (Current Science 75, 103–113; 1998).

High capacity for aerobic glycolysis is an essential characteristic of rapidly growing malignant cells (Baggetto, 1992, Biochimie 74, 959–974, 1992). Methyl glyoxal inactivates glyceraldehyde 3 phosphate dehydrogenase, a key enzyme in the glycolytic pathway, leading to a critical reduction in the levels of ATP in cancerous cells (Ray et al, Molecular & Cellular Biochemistry 177, 21–26,1997). Glyceraldehyde 3 phosphate dehydrogenase catalyzes the phosphorylation of D-glyceraldehyde 3 phosphate to 1,3 biphosphoglycerate. There has been significant literature to suggest the role of glyceraldehyde 3 phosphate dehydrogenase in malignant conditions viz. in lung cancers (Tokunaga et al, 1987, Cancer Research 47, 5616–5619), pancreatic cancers (Schek et al 1988, Cancer research 48, 6354–6359 ), breast cancers (Deasprez et al, 1992, Cancer lett 64, 219–224) and prostate cancers (Epner et al, 1993, Cancer research, 1993, 53, 1995–1997). The kinetics and structure of glyceraldehyde 3 phosphate dehydrogenase enzyme may be critically altered in malignant cells (Bagui et al, 1999, Eur J Biochem 262, 386–395). Glyceraldehyde 3 phosphate dehydrogenase expression is altered in hypoxia (Graven et al, 1994, J. Biol Chem, 269, 24446–24453), in oncogene transformed cells (Persons et al, 1989, Mol. Carcinogenesis, 2, 88–94), and varies with the cell cycle (Mansur et al, 1993, Nucleic Acids Res, 21,993–998). In view of the reported inhibition of glyceraldehyde 3 phosphate dehydrogenase by methyl glyoxal, and its role as a critical glycolytic enzyme altered in malignant cells, we investigated its modulation by the methyl glyoxal conjugates covered in this study.

Egyud and Szent-Gyorgyi showed that methylglyoxal could inhibit tumor development in mice when it was injected into mice along with sarcoma 180 cells (Science 160, 1140; 1968). It was recently demonstrated that methylglyoxal inhibits the proliferation of Ehrlich ascites carcinoma (EAC) cells and leukemia cells. However, the broad spectrum of its anticancer activity has not been investigated so far. Neither is there any report on the antiangiogenic potential of methylglyoxal.

Much work has been carried out on the conjugates of methylglyoxal. U.S. Pat. No. 4,066,650 discloses the addition products between ketoaldehydes and secondary amines. The patent describes method of preparation of the addition products and the pharmaceutical compositions for the treatment of cancer. U.S. Pat. No. 4,238,500 describes the novel condensation products of (α-ketoaldehyde with enediol and their pharmaceutical uses as anticancer, antihypotensive and analgesic compounds. U.S. Pat. No. 5,147,652 describes the liposome encapsulated ketaoaldehydes and their pharmaceutical use for the treatment of cancer and other non-self cells. U.S. Pat. No. 5,849,783 describes the physically and chemically latentiated methylglyoxal or α-ketoaldehydes for treating the non-self cells which includes cancer.

SUMMARY OF THE INVENTION

The present invention relates to the class of novel conjugates of methyl glyoxal with alkyl/aryl esters of imino acid, a process for preparing them and use of these compounds for the treatment of cancer.

DETAILED DESCRIPTION OF THE INVENTION

In the present invention imino acid refers only to pyroglutamic acid. Alkyl and aryl are defined below as substituent $R_1$. The general formula (I) of the novel conjugates and pharmaceutically acceptable salts can be described as shown below.

Structure (I)

where $R_1$ is a $C_1$–$C_{12}$ straight or branched alkyl group benzyl, or phenyl; and where $R_2$ is H, or $COR_3$ where $R_3$ is a $C_1$–$C_6$ straight or branched alkyl group, benzyl or phenyl.

We have for the first time shown the broad spectrum of anticancer activity of methylglyoxal conjugates by demonstrating its in vitro cytotoxicity on cancer of the Colon, Prostate, Larynx, Kidney, Pancreas, Lung, Breast, Intestine, Oral cavity, Ovary, Glioblastoma, and Leukemia. Further, we have demonstrated the in vivo efficacy of methylglyoxal conjugates in tumor xenograft model. Methylglyoxal conjugates are also shown to have antiangiogenic potential. Thus methylglyoxal conjugates not only have a direct cytotoxic effect on cancer cells but also inhibit the growth of cancer by its antiangiogenic activity and the inhibition of the activity of enzyme glyceraldehyde 3 phosphate dehydrogenase. Methylglyoxal conjugates were also tested for acute toxicity in animals. The conjugates were found to be less toxic to animals than methylglyoxal thereby indicating a better tolerability for systemic administration in humans and other mammals. We have prepared methylglyoxal conjugates as a stable dry powder as opposed to methylglyoxal, which is a aqueous solution that is highly reactive and unstable. The conjugates are easier to formulate and have a better shelf life as compared to methylglyoxal.

The present invention provides a pharmaceutical composition of imino acid conjugates of methylglyoxal or pharmaceutically acceptable salts of the imino acid conjugates useful for killing or inhibiting multiplication of cancer cells, preparing novel conjugates of methylglyoxal and testing their bio-activity using cultured human cancer cells as the monitor.

In a preferred embodiment, a pharmaceutically acceptable carrier, diluent, or solvent is used. The invention provides a method of treatment for humans, mammals, or other animals suffering from cancer or other tumors. The method may suitably comprise, consist of, or consist essentially of administering a therapeutically effective dose of the pharmaceutical composition so as to kill or inhibit the multiplication of cancer or tumor cells.

The methods of this invention comprise, consist of, or consist essentially of administering systematically to the mammal a therapeutically effective amount of imino acid conjugates of methylglyoxal. An effective dose of methylglyoxal conjugates or pharmaceutically acceptable salts of the imino acid conjugates ranges from 1 mg/Kg. B. Wt to 300 mg/Kg. B. Wt (preferably 10–100 mg)/Kg. B. Wt) of the mammal, with the dose dependent on the effects sought, the manner of administration, and the cancer being treated. Systemic administration refers to oral, rectal, nasal, transdermal, and parenteral (i.e., intramuscular, intravenous and subcutaneous). In accordance with good clinical practice, it is preferred to administer the composition at a dose that will produce anticancer effects without causing undue harmful side effects. The composition may be administered either alone or as a mixture with other therapeutic agents such as 5-fluorouracil, methotrexate, etoposide, paclitaxel, taxotere, doxorubicin, daunarubicin, vincristine, vinblastine and other such known and established anticancer drugs.

The composition may optionally and preferably contain pharmaceutically acceptable diluents, excipients, solvents, binders, stabilizers, and the like. Such diluents may include: RPMI 1649, buffered saline, isotonic NaCl, Ringer's solution, water, distilled water, polyethylene glycol (neat or in water), 2% Tween in water, dimethyl-sulfoxide to 50% in water, propylene glycol (neat or in water), phosphate buffered saline, balanced salt solution, glycerol, and other conventional fluids that are suitable for intravenous administration. Pharmaceutical composition which provide from about 0.1 to 10 gram (preferably 0.5 to 5.0 gram) of the composition per unit dose are preferred and are conventionally prepared as tablets, lozenges, capsules, powders, aqueous or oily suspension, syrups, elixirs, and aqueous solutions. The nature of the pharmaceutical composition employed will, of course, depend on the desired route of administration.

The invention provides a process for the synthesis of alkyl/aryl ester of pyroglutamic acid, said process comprising:
(a) mixing of pyroglutamic acid, potassium hydrogensulphate and alcohol;
(b) heating the mixture in Microwave (MW) oven with intermittent stirring or heating the mixture to reflux with benzene as co-solvent with continuous stirring;
(c) monitoring the progress of the reaction by TLC;
(d) diluting the reaction mixture with ethyl acetate and filtering out the solid mass;
(e) evaporating the solvent to yield a colourless oil; and
(f) purifying by silica gel column chromatography. The invention also provides a process for preparing a conjugate of methyl glyoxal with alkyl/aryl pyroglutamate, said process comprising:
(a) mixing of alkyl/aryl pyroglutamate, methyl glyoxal and optionally bentonite or clay in Dioxan:water: 2:1;
(b) heating the mixture in MW oven with intermittent stirring or heating to reflux with continuous stirring;
(c) monitoring the reaction by TLC;
(d) diluting the mixture with MeOH and filtering;
(e) concentrating the filtrate in Rotovapor;
(f) removing the residual water as an azeotropic mixture with ethyl acetate; and
(g) purifying by silica gel column chromatography.

The invention also provides a process for preparing acetate of the conjugate of methyl glyoxal-alkyUaryl pyroglutamate, said process comprising:
(a) sonicating a mixture of conjugate of methyl glyoxal-alkyl/aryl pyroglutamate, acetic anhydride and bentonite or clay;
(b) monitoring the reaction by TLC;
(c) diluting with chloroform and filtering the mixture;
(d) concentrating the filtrate in vacuo to yield a crude oily substance; and
(e) purifying by silica gel column chromatography.

Other methods known in the art can be used to prepare the imino acid conjugates of methylglyoxal of formula I.

Pharmaceutically acceptable salts of the imino acid conjugates include the but are not limited to the following: acetate, ascorbate, benzoate, citrate, oxalate, stearate, trifluoroacetate, succinate, tartarate, lactate, fumarate, gluconate, glutamate, phosphate/diphosphate, and valerate. Other salts include Ca, Li, Mg, Na, and K salts, halides, salts of amino acids such as lysine or arginine; guanidine, ammonium, substituted ammonium salts or aluminium salts. The pharmaceutically acceptable salts of the imino acid conjugate may be prepared by methods known in the art.

The present invention is farther described in detail with reference to the following examples, which are given for the purpose of merely illustrating the invention without limiting it.

The advantage of the conjugates over methyglyoxal are their in vitro stability. The stability studies of the conjugates mentioned in the present invention were carried out. The results show that these conjugates are stable at ambient temperature for more than three months.

NMR spectra were recorded in $CDCl_3$ using TMS (0 ppm) as an internal standard on Bruker AVANCE 300. Mass spectra were obtained on Electro Spray Ionisation (ESI)

Mass Spectrometer (Hewlett Packard 1100 LC MSD). IR spectra were recorded using FTIR apparatus (Nicolet FTIR Model 740). TLC plate was performed on a precoated silica gel plate developed with $CHCl_3$/MeOH, 10/1 exposed to iodine vapors or stained with 2,4-Dinitrophenyl hydrazine solution.

In the NMR spectra of the conjugates and their corresponding acetates was also seen a set of singlets belonging to the methyl protons of the N-side chain and the acetoxyl group in the region between δ 2.65 and 2.0 where the four methylene protons of the pyrrolidone ring resonate. Their values have been mentioned at the suitable places.

General methods of preparation of alkyvaryl ester of pyroglutamic acid

Method-1

Approximately 2.58 g (20 mmol) of pyroglutamic acid, approximately 2.72 g (20 mmol) of potassium hydrogensulphate and alcohol (200 mmol) were taken in 100 ml beaker and sonicated for about five minutes. The resultant mixture was exposed to MW (175 watts) for about ten minutes in small installments of 30 seconds with intermittent manual stirring. The mixture was then diluted with ethylacetate and filtered. The solution was concentrated in Rotavapor to yield a colourless oil, which upon chromatography over silica gel column furnished alkyl/aryl ester of pyroglutamic acid in about 90% yield.

Method-2

Approximately 2.58 g (20 mmol) of pyroglutamic acid, approximately 2.72 g (20 mmol) of potassium hydrogensulphate, alcohol (200 mmol) and benzene (50 ml) were taken in 100 ml round bottom flask equipped with a reflux condenser and heated to reflux in an oil bath for 4–5 hours followed by distillation of the solvents. The residue was diluted with ethylacetate and filtered. The organic solvent was removed in Rotavapor to yield a crude colourless oil which upon chromatography over silica gel column furnished alkyl/aryl ester of pyroglutamic acid in about 90% yield.

Following either of the above mentioned methods methyl, butyl and benzyl esters of pyroglutamic acid were synthesised and the formation of the desired products was confirmed by NMR ($^1$H and $^{13}$C, 300 MHz), IR and Mass spectra.

General methods of preparation of conjugate of methyl glyoxal with alkyl/aryl ester of pyroglutamic acid

Method-1

Alkyl/aryl ester of pyroglutamic acid (10 mmol), 40% solution of methyl glyoxal (20 mmol), bentonite (weight equivalent to that of the starting ester) and about 25 ml of 2:1 mixture of dioxan : water were taken in a beaker, sonicated for two minutes and exposed to MW (175 watt) for about eight minutes in small installments of 30 seconds with intermittent manual stirring. The mixture was diluted with methanol and filtered. The solution was concentrated and the residual water was removed as an azeotropic mixture with ethyl acetate to yield a viscous oil, which upon chromatography over silica gel column furnished the desired product, the conjugate of methyl glyoxal-alkyl/aryl pyroglutamate in about 30% yield.

Method-2

Alkyl/aryl ester of pyroglutamic acid (10 mmol), 40% solution of methyl glyoxal (20 mmol), bentonite (weight equivalent to that of the starting ester) and about 25 ml of 2:1 mixture of dioxan : water were taken an a round bottom flask equipped with a reflux condenser and heated to reflux in an oil bath for about five hours. After cooling the reaction mixture to room temperature, it was diluted with methanol and filtered. The solution was concentrated and the residual water was removed as an azeotropic mixture with ethyl acetate to yield a viscous oil, which upon chromatography over silica gel column furnished the desired product, the conjugate of methyl glyoxal-alkyl/aryl pyroglutamate in about 27% yield.

It was also observed that the above reactions did proceed without bentonite. The presence of bentonite resulted in better yield and neater reaction.

Following either of the protocols mentioned above for preparation of conjugate of methyl glyoxal with alkyl/aryl ester of pyroglutamic acid, the three conjugates of methyl glyoxal with the methyl, butyl and benzyl pyroglutamates were prepared. The NMR and TLC of these samples revealed the formation 1:1 mixture two stereoisomers. The mixture of the stereoisomers was taken as such for further studies.

The structures, codes and spectral details of these conjugates are given below:

N-(1-Hydroxy-2-ketopropyl)-methylpyroglutamate (MGC-1)

$^1$H NMR: δ 5.8–5.1 (1H, two doublets at 5.75 & 5.16 in the ratio 1:1), 4.8–4.2 (2H, m), 3.8–3.6 (3H, two singlets at 3.80 & 3.69 in the ratio 1:1), 2.65–2.2 (7H, m, also seen is a singlet at 2.34 for methyl protons of N-side chain); MS: 216 [MH$^+$], 238 [MNa$^+$]; IR (neat, ν cm$^{-1}$): 3462, 1722, 1707, 1680, 1205, 1016.

N-(1-Hydroxy-2-ketopropyl)-butylpyroglutamate (MGC-2)

$^1$H NMR: δ 5.8–5.1 (1H, two doublets at 5.74 & 5.15 in the ratio 1:1), 4.5–4.0 (4H, m), 2.65–2.0 (7H, m, also seen are two singlets at 2.35 & 2.34 in the ratio 1:1 for methyl protons of N-side chain), 1.7–1.5 (2H, m), 1.45–1.25 (2H, m), 1.0–0.9 (3H, m); MS:258 [MH$^+$]; IR (neat, ν cm$^{-1}$): 3424, 1738, 1692, 1185.

N-(1-Hydroxy-2-ketopropyl)-benzylpyroglutamate (MGC-3)

¹H NMR: δ 7.5–7.3 (5H, m), 5.75–5.1 (1H, two doublets at 5.73 & 5.18 in the ratio 1:1), 5.10 (2H, s), 4.5–4.3 (1H, two multiplets at 4.45 & 4.36 in the ratio 1:1), 4.27 (1H, d), 2.60–2.34 (7H, m, also seen are two singlets at 2.30 & 2.28 in the ratio 1:1 for methyl protons of N-side chain); MS: 292 [MH⁺], 314 [MNa⁺], 330 [MK⁺]; IR (neat, ν cm⁻¹): 3424, 1738, 1692, 1185

N-(1-Hydroxy-2-ketopropyl)-ethylpyroglutamate (MGC-7)

¹H NMR: δ 5.8–5.1 (1H, two doublets at 5.75 & 5.17 in the ratio 1:1), 4.6–4.0 (4H, m), 2.7–2.0 (7H, m, also seen are two singlets at 2.35 & 2.34 in the ratio 1:1 for methyl protons of N-side chain), 1.35–1.20 (3H, m); MS: 230 [MH⁺], 252 [MNa⁺]; IR (neat, ν cm⁻¹): 3370, 1736, 1701, 1200.

General method of preparation of acetate of conjugate of methyl glyoxal with alkyl/aryl ester of pyroglutamic acid.

A mixture of conjugate of methyl glyoxal-alkyl/aryl pyroglutamate (10 mmol), acetic anhydride (about 4 ml) and bentonite (weight equivalent to that of the conjugate) was sonicated for one hour under anhydrous conditions. The resultant mixture was diluted with chloroform and filtered. The solvents were evaporated in vacuo to furnish an oily substance which was chromatographed through silica gel column to give the desired acetate in about 85% yield.

Following this procedure the acetates of four conjugates MGC-1, MGC-2, MGC-3 and MGC-7 were prepared. The NMR and TLC of these samples revealed the formation 1:1 mixture two stereoisomers. The mixture of the stereoisomers was taken as such for further studies.

The structures, codes and spectral details of these acetates are given below:

N-(1-Acetoxy-2-ketopropyl)-methylpyroglutamate (MGC-4)

¹H NMR δ 6.6–6.3 (1H, two singlets at 6.53 & 6.36 in the ratio 1:1), 4.5–4.2 (1H, two multiplets at 4.41 & 4.32 in the ratio 1:1), 3.9–3.6 (3H, two singlets at 3.79 & 3.71 in the ratio 1:1), 2.65–2.0 (10H, m, also seen are two singlets at 2.290 & 2.287 in the ratio 1:1 for methyl protons of N-side chain and two singlets at 2.14 & 2.13 in the ratio 1:1 for methyl protons of acetoxyl group); MS: 258 [MH⁺], 380 [MNa⁺]; IR (neat, ν cm⁻¹): 1736, 1718, 1200.

N-(1-Acetoxy-2-ketopropyl)-butylpyroglutamate (MGC-5)

¹H NMR: δ 6.6–6.3 (1H, two singlets at 6.51 & 6.32 in the ratio 1:1), 4.45–4.25 (1H, two multiplets at 4.37 & 4.29 in the ratio 1:1), 4.25–4.0 (2H, two multiplets at 4.15 & 4.09 in the ratio 1:1) 2.65–2.0 (10H, m, also seen are singlet 2.27 for methyl protons of N-side chain and two singlets at 2.13 & 2.11 in the ratio 1:1 for methyl protons of acetoxyl group), 1.75–1.55 (2H, m), 1.5–1.25 (2H, m), 1.05–0.85 (3H, m); MS: 300 [MH⁺], 322 [MNa⁺], 338 [MK⁺]; IR (neat, ν cm⁻¹): 1738, 1720,1631, 1200.

N-(1-acetoxy-2-ketopropyl)-benzylpyroglutamate (MGC-6)

Melting point: 83–84° C.; ¹H NMR: δ 7.40–7.32 (5H, m), 6.6–6.3 (1H, two singlets at 6.52 & 6.36 in the ratio 1:1), 5.3–5.1 (2H, two singlets at 5.21 & 5.12 in the ratio 1:1), 4.5–4.3 (1H, two multiplets at 4.38 & 4.35 in the ratio 1:1), 2.6–2.0 (10H, m, also seen are two singlets at 2.24 & 2.23 in the ratio 1:1 for methyl protons of N-side chain and two singlets at 2.10 & 2.03 in the ratio 1:1 for methyl protons of acetoxyl group); MS : 334 [MH⁺], 358 [MNa⁺]; IR (neat, ν cm⁻¹): 1736, 1697, 1375, 1219, 1039.

N-(1-Acetoxy-2-ketopropyl)-ethylpyroglutarnate (MGC-8)

¹H NMR: δ 6.55–6.30 (1H, two singlets at 6.53 & 6.34 in the ratio 1:1), 4.5–4.1 (3H, m), 2.65–2.05 (10H, m, also seen are singlet 2.29 for methyl protons of N-side chain and two singlets at 2.13 & 2.12 in the ratio 1:1 for methyl protons of acetoxyl group), 1.75–1.2 (3H, m); MS: 272 [MH⁺]; IR (neat, ν cm⁻¹): 1738, 1707, 1196.

EXAMPLE 1

Methylglyoxal conjugates were tested for cytotoxicity against 12 human tumor cell lines. A comparison of cytotoxicity was carried out with methylglyoxal. Briefly, a three day MTT cytotoxicity assay was performed, which is based on the principle of uptake of MTT (3-(4,5-dimethylthiazol-2-yl)-2,5-diphenyl tetrazolium bromide), a tetrazolium salt, by the metabolically active cells where it is metabolized by active mitochondria into a blue colored formazan product that is read spectrophotometrically. MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. For each type of tumor cell, 20,000 to 50,000 cells were seeded in a 96-well culture plate and incubated with the combination in a $CO_2$ incubator for 24 hours. The final concentration range of methylglyoxal and its conjugates was 1 to 10 nM. Control cells not treated with methylglyoxal or its conjugates were similarly incubated. The assay was terminated after 24 hours by adding 100 ug (20 ul) of MTT to each well, then incubating for additional one hour, and finally adding 50 ul of 10% SDS-1.01N HCl to each well to lyse the cells and dissolve formazan. After incubating for one hour, the plate was read spectrophotometrically at 540 nm and the percentage cytotoxicity calculated. Tables 1 to 8 show the dose response of Methylglyoxal conjugates MGC-1 to 8. While the dose response studies were done in 12 cell lines listed in Table 9, the data is presented in Tables 1 to 8 is representative of all the cell lines screened. Table 9 shows the comparative $ED_{50}$ values of cytotoxicity of Methylglyoxal conjugates MGC-1 to 8 with methylglyoxal.

TABLE 1

Percent Cytotoxicity Of MGC-1 On Human Tumor Cell Lines

| Cell lines | Percent cytotoxicity of MGC-1 on human tumor cell lines | | | | |
|---|---|---|---|---|---|
| | 1.0 mM | 2.5 mM | 4 mM | 5 mM | 10 mM |
| MOLT 4 Leukemia | 23.4 ± 2.7 | 57.9 ± 3.9 | 78.9 ± 5.5 | 85.9 ± 6.5 | 88.5 ± 3.8 |
| PA 1 Ovary | 35.8 ± 3.8 | 59.6 ± 4.3 | 84.9 ± 4.9 | 88.6 ± 4.8 | 90.3 ± 5.9 |
| PTC Colon | 23.0 ± 2.1 | 43.9 ± 4.9 | 55.6 ± 3.9 | 87.8 ± 5.3 | 88.0 ± 2.9 |
| Miapaca2 Pancreas | 2.9 ± 0.2 | 23.9 ± 2.9 | 48.9 ± 3.6 | 67.9 ± 2.9 | 85.0 ± 4.5 |
| DU145 Prostate | 43.9 ± 4.7 | 60.9 ± 4.9 | 88.7 ± 5.9 | 87.3 ± 5.9 | 88.4 ± 5.2 |
| L132 Lung | 0.0 ± 0.0 | 3.9 ± 0.0 | 10.6 ± 1.9 | 12.9 ± 1.9 | 34.9 ± 3.9 |
| MCF7 breast | 0.0 ± 0.0 | 0.0 ± 0.0 | 2.9 ± 0.0 | 12.9 ± 2.1 | 21.9 ± 2.1 |

TABLE 2

Percent Cytotoxicity Of MGC-2 On Human Tumor Cell Lines

| Cell lines | Percent cytotoxicity of MGC-2 on human tumor cell lines | | | | |
|---|---|---|---|---|---|
| | 1.0 mM | 2.5 mM | 4 mM | 5 mM | 10 mM |
| MOLT 4 Leukemia | 75.9 ± 4.8 | 85.9 ± 6.3 | 87.8 ± 5.0 | 88.2 ± 5.9 | 90.2 ± 7.2 |
| PA 1 Ovary | 54.7.8 ± 3.9 | 57.9 ± 4.5 | 67.9 ± 5.4 | 84.9 ± 4.8 | 87.9 ± 6.3 |
| PTC Colon | 45.8 ± 5.3 | 68.9 ± 5.3 | 85.9 ± 6.2 | 88.8 ± 5.3 | 86.9 ± 5.0 |
| Miapaca2 Pancreas | 34.8 ± 4.9 | 64.9 ± 5.9 | 74.9 ± 3.8 | 76.9 ± 4.0 | 84.9 ± 6.3 |
| DU145 Prostate | 43.9 ± 2.6 | 53.9 ± 3.8 | 58.9 ± 4.3 | 67.9 ± 5.2 | 86.9 ± 6.9 |
| L132 Lung | 34.8 ± 4.9 | 58.5 ± 3.6 | 62.9 ± 2.9 | 87.8 ± 5.8 | 88.6 ± 3.0 |
| MCF7 breast | 34.7 ± 2.4 | 50.6 ± 4.1 | 57.9 ± 4.8 | 67.9 ± 4.0 | 78.9 ± 5.2 |

TABLE 3

Percent Cytotoxicity Of MGC-3 On Human Tumor Cell Lines

| Cell lines | Percent cytotoxicity of MGC-3 on human tumor cell lines | | | | |
|---|---|---|---|---|---|
| | 1.0 mM | 2.5 mM | 4 mM | 5 mM | 10 mM |
| MOLT 4 Leukemia | 42.1 ± 4.3 | 54.9 ± 4.3 | 65.9 ± 4.3 | 87.9 ± 7.3 | 88.3 ± 7.4 |
| PA 1 Ovary | 42.8 ± 4.9 | 64.8 ± 5.9 | 66.9 ± 5.9 | 78.9 ± 7.4 | 88.5 ± 8.4 |
| PTC Colon | 0.0 ± 0.0 | 32.9 ± 3.8 | 54.9 ± 3.8 | 56.8 ± 5.7 | 86.9 ± 7.6 |
| Miapaca2 Pancreas | 0.0 ± 0.0 | 0.0 ± 0.0 | 0.0 ± 0.0 | 12.9 ± 1.0 | 14.1 ± 1.9 |
| DU145 Prostate | 29.4 ± 4.2 | 56.9 ± 4.3 | 64.8 ± 6.3 | 87.9 ± 8.3 | 88.4 ± 4.0 |
| L132 Lung | 0.0 ± 0.0 | 30.0 ± 2.9 | 45.8 ± 4.5 | 52.9 ± 5.2 | 79.4 ± 5.9 |
| MCF7 breast | 0.0 ± 0.0 | 0.0 ± 0.0 | 0.0 ± 0.0 | 2.7 ± 0.1 | 12.4 ± 1.0 |

TABLE 4

Percent Cytotoxicity Of MGC-4 On Human Tumor Cell Lines

| Cell lines | Percent cytotoxicity of MGC-4 on human tumor cell lines | | | | |
|---|---|---|---|---|---|
| | 1.0 mM | 2.5 mM | 4 mM | 5 mM | 10 mM |
| MOLT 4 Leukemia | 36.9 ± 3.9 | 57.9 ± 3.1 | 78.9 ± 4.9 | 88.4 ± 7.5 | 85.9 ± 7.3 |
| PA 1 Ovary | 28.9 ± 3.2 | 67.9 ± 4.9 | 87.9 ± 6.4 | 88.6 ± 6.9 | 88.0 ± 6.9 |
| PTC Colon | 23.9 ± 3.0 | 39.0 ± 5.2 | 56.9 ± 5.9 | 84.2 ± 7.4 | 87.3 ± 6.0 |
| Miapaca2 Pancreas | 0.0 ± 0.0 | 3.9 ± 0.5 | 46.8 ± 4.9 | 57.9 ± 5.9 | 79.4 ± 4.8 |
| DU145 Prostate | 28.9 ± 4.2 | 58.9 ± 4.9 | 82.1 ± 7.3 | 85.6 ± 7.3 | 87.9 ± 7.3 |
| L132 Lung | 0.0 ± 0.0 | 0.0 ± 0.0 | 0.0 ± 0.0 | 4.9 ± 0.6 | 37.9 ± 3.5 |
| MCF7 breast | 0.0 ± 0.0 | 0.0 ± 0.0 | 3.8 ± 0.4 | 23.8 ± 0.8 | 31.9 ± 2.9 |

TABLE 5

Percent Cytotoxicity Of MGC-5 On Human Tumor Cell Lines

| Cell lines | Percent cytotoxicity of MGC-5 on human tumor cell lines | | | | |
|---|---|---|---|---|---|
| | 1.0 mM | 2.5 mM | 4 mM | 5 mM | 10 mM |
| MOLT 4 Leukemia | 25.9 ± 2.9 | 61.0 ± 4.8 | 76.0 ± 7.1 | 82.9 ± 6.9 | 87.9 ± 6.9 |
| PA 1 Ovary | 31.8 ± 3.1 | 58.8 ± 5.3 | 83.9 ± 7.8 | 85.9 ± 6.2 | 86.9 ± 8.4 |

TABLE 5-continued

Percent Cytotoxicity Of MGC-5 On Human Tumor Cell Lines

Percent cytotoxicity of MGC-5 on human tumor cell lines

| Cell lines | 1.0 mM | 2.5 mM | 4 mM | 5 mM | 10 mM |
|---|---|---|---|---|---|
| PTC Colon | 2.9 ± 0.3 | 37.9 ± 3.9 | 53.9 ± 5.4 | 85.9 ± 8.9 | 89.2 ± 7.4 |
| Miapaca2 Pancreas | 0.0 ± 0.0 | 24.8 ± 2.6 | 43.8 ± 3.9 | 54.9 ± 4.2 | 67.9 ± 4.0 |
| DU145 Prostate | 27.9 ± 0.4 | 58.4 ± 5.9 | 59.0 ± 4.3 | 68.3 ± 4.6 | 80.0 ± 7.0 |
| L132 Lung | 2.9 ± 0.1 | 36.9 ± 4.9 | 57.8 ± 4.0 | 59.0 ± 6.0 | 76.3 ± 5.4 |
| MCF7 breast | 0.0 ± 0.0 | 0.0 ± 0.0 | 34.9 ± 3.9 | 51.9 ± 3.8 | 58.7 ± 5.0 |

TABLE 6

Percent Cytotoxicity Of MGC-6 On Human Tumor Cell Lines

Percent cytotoxicity of MGC-6 on human tumor cell lines

| Cell lines | 1.0 mM | 2.5 mM | 4 mM | 5 mM | 10 mM |
|---|---|---|---|---|---|
| MOLT 4 Leukemia | 41.9 ± 4.2 | 61.9 ± 5.3 | 84.9 ± 7.4 | 84.8 ± 3.9 | 87.1 ± 6.8 |
| PA 1 Ovary | 42.9 ± 4.9 | 63.9 ± 4.9 | 86.9 ± 6.9 | 88.7 ± 5.9 | 84.0 ± 7.5 |
| PTC Colon | 38.9 ± 3.9 | 59.7 ± 5.3 | 75.9 ± 4.0 | 80.6 ± 7.4 | 86.4 ± 4.0 |
| Miapaca2 Pancreas | 0.0 ± 0.0 | 23.7 ± 2.0 | 51.9 ± 5.2 | 58.5 ± 5.0 | 67.4 ± 3.0 |
| DU145 Prostate | 37.8 ± 2.6 | 56.9 ± 4.2 | 78.9 ± 7.4 | 81.5 ± 7.3 | 85.9 ± 6.9 |
| L132 Lung | 2.7 ± 0.2 | 34.8 ± 5.8 | 53.9 ± 5.0 | 67.9 ± 5.0 | 74.7 ± 7.3 |
| MCF7 breast | 0.0 ± 0.0 | 0.0 ± 0.0 | 0.0 ± 0.0 | 13.9 ± 1.1 | 23.9 ± 2.9 |

TABLE 7

Percent Cytotoxicity Of MGC-7 On Human Tumor Cell Lines

Percent cytotoxicity of MGC-7 on human tumor cell lines

| Cell lines | 1.0 mM | 2.5 mM | 4 mM | 5 nM | 10 mM |
|---|---|---|---|---|---|
| MOLT 4 Leukemia | 39.4 ± 2.7 | 58.5 ± 3.8 | 59.1 ± 4.3 | 64.3 ± 4.9 | 73.4 ± 2.0 |
| PA 1 Ovary | 45.6 ± 1.9 | 58.4 ± 4.7 | 65.5 ± 3.9 | 79.9 ± 5.2 | 84.9 ± 5.4 |
| PTC Colon | 34.3 ± 1.9 | 54.3 ± 4.9 | 65.9 ± 4.8 | 78.2 ± 3.9 | 82.2 ± 6.1 |
| Miapaca2 Pancreas | 0 ± 0 | 28 ± 1.5 | 89 ± 2.3 | 88 ± 4.1 | 85 ± 4.1 |
| DU145 Prostate | 56.0 ± 5.9 | 65.0 ± 2.9 | 78.4 ± 6.9 | 83.0 ± 4.9 | 89.0 ± 6.1 |
| L132 Lung | 0 ± 0 | 0 ± 0 | 0 ± 0 | 0 ± 0 | 0 ± 0 |
| MCF7 breast | 7 ± 1.3 | 10 ± 2.5 | 69 ± 3.2 | 85 ± 4.5 | 83 ± 4.5 |

TABLE 8

Percent Cytotoxicity Of MGC-8 On Human Tumor Cell Lines

Percent cytotoxicity of MGC-8 on human tumor cell lines

| Cell lines | 1.0 mM | 2.5 mM | 4 mM | 5 mM | 10 mM |
|---|---|---|---|---|---|
| MOLT 4 Leukemia | 40.3 ± 2.9 | 58.3 ± 4.9 | 65.0 ± 5.9 | 75.2 ± 2.9 | 81.9 ± 5.2 |
| PA 1 Ovary | 38.0 ± 3.7 | 56.0 ± 4.8 | 64.5 ± 5.3 | 69.0 ± 2.1 | 71.7 ± 6.3 |
| PTC Colon | 32.2 ± 3.9 | 48.6 ± 2.9 | 67.7 ± 4.8 | 76.3 ± 1.0 | 79.6 ± 3.0 |
| Miapaca2 Pancreas | 0 ± 0 | 61 ± 2.5 | 89 ± 4.5 | 88 ± 4.5 | 86 ± 5.0 |
| DU145 Prostate | 43.0 ± 3.8 | 67.4 ± 5.2 | 69.9 ± 7.9 | 73.5 ± 3.0 | 79.3 ± 1.9 |
| L132 Lung | 8 ± 1.5 | 12 ± 3.3 | 25 ± 3.5 | 35 ± 4.1 | 45 ± 5.1 |
| MCF7 breast | 16 ± 4.1 | 36 ± 3.5 | 70 ± 4.5 | 73 ± 6.0 | 87 ± 7.0 |

TABLE 9

$ED_{50}$ Values Of Cytotoxicity Of Methylglyoxal Conjugates Against Various Human Tumor Cell Lines $ED_{50}$ VALUES (mM)

| S.NO | CELL LINE | Methylglyoxal | MGC1 | MGC2 | MGC3 | MGC4 | MGC5 | MGC6 | MGC7 | MGC8 |
|---|---|---|---|---|---|---|---|---|---|---|
| 1 | U87MG Glioblastoma | 1.95 ± 0.7 | 2.25 ± 0.5 | 3.15 ± 1.1 | >5 | 2.4 ± 0.5 | 3.4 ± 1.1 | 4.78 ± 0.6 | 1.84 ± 0.6 | 1.88 ± 0.7 |
| 2 | KB Oral | 0.9 ± 0.2 | 1.7 ± 0.5 | 2.6 ± 0.5 | 2.55 ± 0.4 | 1.55 ± 0.3 | 2 ± 0.7 | 2.95 ± 0.3 | 1.85 ± 0.6 | 1.95 ± 0.8 |
| 3 | PTC Colon | 0.7 ± 0.1 | 3.7 ± 1.4 | 1.6 ± 0.1 | 3.8 ± 0.7 | 3.8 ± 1.1 | 3.8 ± 0.9 | 1.6 ± 0.4 | 2.4 ± 0.5 | 2.75 ± 0.4 |
| 4 | DU145 Prostate | 1.5 ± 0.6 | 1.7 ± 0.6 | 1.6 ± 0.1 | 1.8 ± 0.2 | 1.8 ± 0.3 | 1.9 ± 0.7 | 1.9 ± 1.0 | 0.85 ± 0.3 | 1.3 ± 0.3 |
| 5 | Hep2 Larynx | 2.6 ± 0.4 | 2.2 ± 0.4 | 2.0 ± 0.3 | 2.6 ± | 3.2 ± 0.8 | 1.9 ± | 1.2 ± 0.2 | 2.5 ± 1.1 | 2.1 ± 0.6 |
| 6 | 293 Kidney | 3.8 ± 1.1 | 2.2 ± 1.6 | 2.0 ± 0.8 | 2.0 ± 0.3 | 1.4 ± 0.1 | 1.9 ± 0.7 | 2.9 ± 1.0 | 3.1 ± 1.3 | 2.9 ± 0.5 |

TABLE 9-continued

ED$_{50}$ Values Of Cytotoxicity Of Methylglyoxal Conjugates Against Various Human Tumor Cell Lines ED$_{50}$ VALUES (mM)

| S.NO | CELL LINE | Methylglyoxal | MGC1 | MGC2 | MGC3 | MGC4 | MGC5 | MGC6 | MGC7 | MGC8 |
|---|---|---|---|---|---|---|---|---|---|---|
| 7 | Miapaca2 Pancreas | 0.7 ± 0.1 | 4.2 ± 1.3 | 1.7 ± 0.6 | >5 | 4.2 ± 1.1 | 4.3 ± 1.6 | 3.9 ± 1.0 | 2.4 ± 1.0 | 1.8 ± 0.9 |
| 8 | L132 Lung | <1.0 | >5 | 1.9 ± 0.8 | 4.6 ± 1.6 | >5 | 3.6 ± 1.1 | 3.8 ± 1.0 | >5 | >5 |
| 9 | MCF7 Breast | 1.8 ± 0.6 | >5 | 2.5 ± 0.4 | >5 | >5 | 5.0 ± 2.1 | >5 | 2.8 ± 1.1 | 2.4 ± 1.2 |
| 10 | INT 407 Intestine | 1.8 ± 0.7 | 2.9 ± 0.5 | 2.7 ± 0.8 | 2.85 ± 0.7 | 2.3 ± 1.1 | 2.6 ± 1.1 | >5 | 2.7 ± 1.2 | 0.55 ± 0.3 |
| 11 | Molt 4 Leukemia | 0.8 ± 0.2 | 1.5 ± 0.4 | <1 | 1.65 ± 0.5 | 1.5 ± 0.2 | 1.5 ± 0.1 | 1.3 ± 0.3 | 1.5 ± 0.2 | 2.9 ± 0.5 |
| 12 | PA 1 Ovarian | 3.6 ± 0.3 | 1.5 ± 0.4 | 1.2 ± 0.2 | 1.8 ± 0.6 | 1.6 ± 0.2 | 1.6 ± 0.1 | 1.4 ± 0.2 | 1.2 ± 0.2 | 1.8 ± 0.7 |

EXAMPLE 2

The activity of Glyceraldehyde 3 phosphate dehydrogenase enzyme was assayed by the methods detailed earlier. (Krebs E, 1955, Methods in Enzymology, 1 407 and Velick S, 1955, Methods in Enzymology, 1, 401). To monitor the reaction, the increase in absorbance at 340 nm due to the formation of NADH from NAD was recorded at 15 seconds intervals, the values remaining almost linear for 3 minutes. The assay mixture was in a total volume of 1.5 ml containing 1.3 ml of Sodium pyrophosphate buffer (0.015M; pH 8.5), containing sodium arsenate (0.03M), 0.05 ml of NAD (7.5 mM), 0.05 ml of DTT (0.1M) and 0.05 ml of DL- glyceraldehyde 3 phosphate (7 mM). The enzyme was diluted 1:100 immediately prior to use in Sodium pyrophosphate buffer (0.015M) (pH 8.5) containing sodium arsenate (0.03M). The reaction was initiated by the addition of 0.05 ml of glyceraldehyde 3 phosphate dehydrogenase enzyme. The test mixture contained methyl glyoxal or its conjugates in concentrations ranging from 0.5 mM to 5 mM. Methyl glyoxal and its conjugates were dissolved in 2.5% ethanol and water. The control experiments were carried out in the absence of the enzyme or the substrate under identical conditions. One unit of activity of glyceraldehyde 3 phosphate dehydrogenase is defined as the amount of enzyme required to convert 1umol of NAD to NADH per minute under conditions defined as above. The inhibition of activity of glyceraldehyde 3 phosphate dehydrogenase enzyme by Methylglyoxal and its conjugates was calculated. Table 10 shows that Glyceraldehyde 3 phosphate dehydrogenase enzyme activity is inhibited significantly by methyl glyoxal and its conjugates, in concentration ranging from 0.5 mM to 5 mM.

TABLE 10

Percent Inhibition Of Glyceraldehyde 3 Phosphate Dehydrogenase Activity By Methyl Glyoxal And Its Conjugates

| Conjugate | 0.5 mM | 1 mM | 5 mM |
|---|---|---|---|
| Methyl glyoxal | 15 ± 4 | 18 ± 3.4 | 20 ± 4.0 |
| MGC1 | 30.9 ± 2.7 | 34.5 ± 3.1 | 36.2 ± 1.2 |
| MGC2 | 23.6 ± 2.8 | 29 ± 1.8 | 38.1 ± 1.1 |
| MGC4 | 21.6 ± 3 | 28.5 ± 2.5 | 31.6 ± 3.5 |
| MGC6 | 28.3 ± 2.5 | 29.4 ± 3.0 | 30.1 ± 4.0 |
| MGC7 | 9.1 ± 2.6 | 14.2 ± 2.3 | 12.8 ± 1.7 |
| MGC8 | 32.8 ± 1.2 | 40.1 ± 2.2 | 38.2 ± 1.9 |

EXAMPLE 3

The antitumor activity of Methylglyoxal and MGC-4 given orally on PTC (Colon) Tumor Xenografts grown in nude mice.

PTC (colon) tumor xenografts were initiated in Balb/c athymic mice by subcutaneous inoculation of a single cell suspension of PTC cells (15×10$^6$ cells/100 μL). The drugs to be tested (Methylglyoxal (40% aqueous solution), MGC-4 (Synthesized) were prepared at a concentration of 20 mg/ml so as to deliver a dose of 10 mg per 500 μl. When the average tumor volume reached around 900 mm$^3$ the tumor-bearing mice were divided into three groups of 3 animals each. One of the groups was randomly assigned for MGC-4 treatment, the other group was assigned for treatment with Methylglyoxal while the third group served as untreated control. 500 μl of the drug was administered to the treatment group of tumor bearing animals orally using oral gavage tube once a day for 15 days. The anti-tumor activity was monitored by measuring tumor volumes every fourth day and calculating volumes using the formula 0.4×W$^2$×L(W=smaller dia, L=larger dia,).

Figure 1:
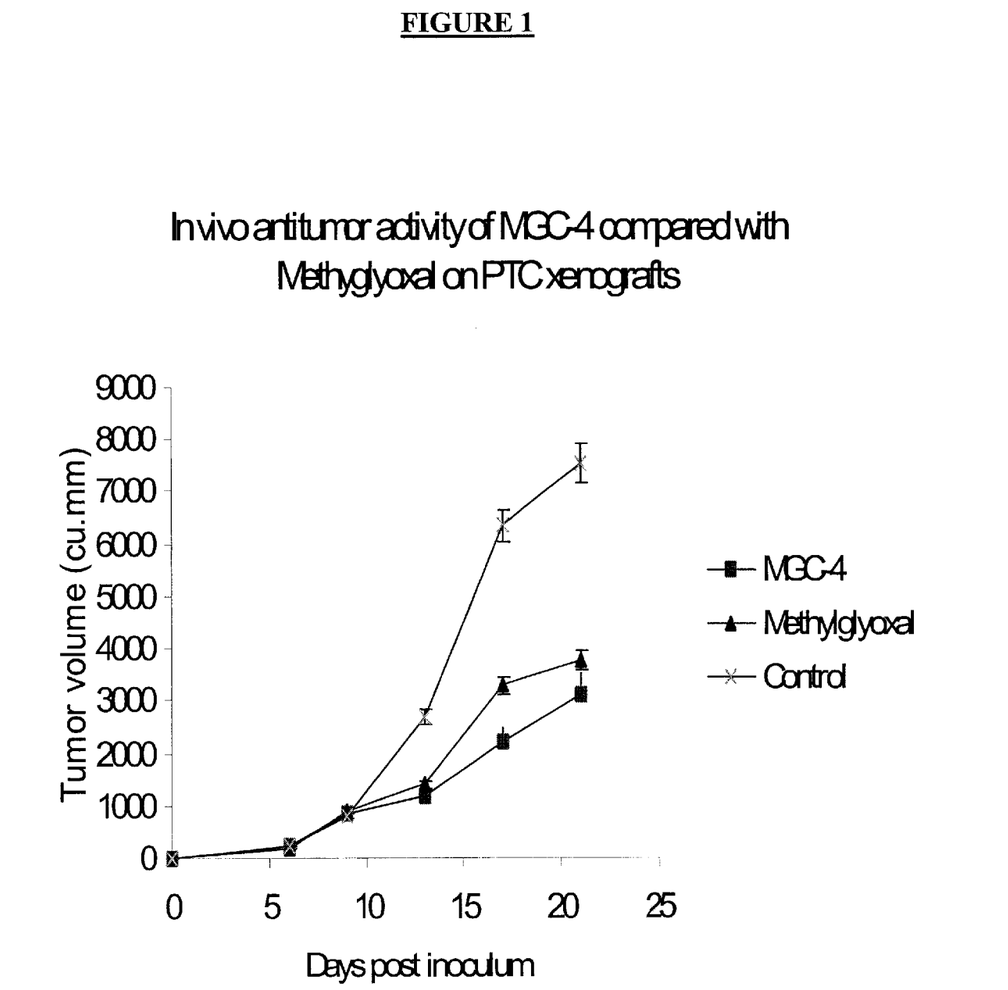
FIG. 1 shows the pattern of tumor growth in treated and control tumor xenografts.

FIG. 1 shows the pattern of tumor growth in both treated and control tumor xenografts.

Treated tumors show delayed tumor growth following two weeks of treatment. At the end of treatment the average tumor volume of Methylglyoxal treated tumors was 50% and MGC-4 treated tumors was 41% as compared to average tumor volume of untreated control tumors.

EXAMPLE 4

Inhibition of "Tube-Like-Structure" (TLS) Activity by Methylglyoxal and its Conjugates Matrigel (70 ul) was placed into each well of a 96-well culture plate at 4° C. and was allowed to polymerize by incubation at 37° C. for 30 min. ECV304 (1×10$^4$) cells were seeded on the Matrigel in 200 ul DMEM supplemented with 10% FBS. The compounds to be tested were added to marked wells at selected non-cytotoxic concentrations and incubated at 37° C. for 24 hours. Five different phase-contrast microscopic fields (4X) were viewed and tube-like structure formation was evaluated qualatively by observing formation of lumen (sprouting) and extent of formation of branches and loops by sprouts (intususception). The inhibition of TLS caused by the addition of the test compound was recorded as significant (++), marginal (+), or no effect (−) as compared to the control TLS formation. A summary of the results is given below in the form of a table indicating the concentrations tested. Compounds MGC-3, MGC-1, MGC-5, and MGC-2 show marginal to significant anti-TLS activity and are comparable with Methylglyoxal.

TABLE 11

Tls Inhibition By Mg And Its Derivatives

| S No. | Molecule | Conc. | TLS Inhibition (Qualitative) |
|---|---|---|---|
| 1 | Methylglyoxal | 0.5 mM | + |
| 2 | Methylglyoxal | 0.8 mM | + |
| 3 | Methylglyoxal | 1 mM | ++ |
| 4 | MGC-1 | 1.2 mM | + |
| 5 | MGC-1 | 1.5 mM | + |
| 6 | MGC-2 | 1.2 mM | + |
| 7 | MGC-2 | 1.5 mM | ++ |
| 8 | MGC-3 | 2 mM | + |
| 9 | MGC-3 | 2.5 mM | ++ |
| 10 | MGC-4 | 1.2 mM | − |
| 11 | MGC-4 | 1.5 mM | − |
| 12 | MGC-5 | 1.2 mM | + |
| 13 | MGC-5 | 1.5 mM | + |
| 14 | MGC-6 | 1.2 mM | − |
| 15 | MGC-6 | 1.5 mM | − |

+: Marginal inhibition of sprouting and intususception
++: Significant inhibition of sprouting and intususception

EXAMPLE 5

Acute Toxicity of Methylglyoxal and its Conjugates in Mice

The therapeutic dose of methylglyoxal and its conjugates has been determined to be 10 mg per mouse given by oral route. Since most anti-cancer drugs have very low therapeutic indices, we determined the therapeutic index of methylglyoxal and its conjugates in mice.

Acute toxicity studies were performed using the oral route of administration. 5 dose levels (2.5X, 3.5X, 5X, 7.5X, 10X; X=400 mg/kg B.Wt.) were given to elicit a range of response to treatment in order to assess the $LD_{10}$ and $LD_{50}$ values.

A batch of 5 female and 5 male mice each was administered the test substance by oral route. To administer exact amounts of the test substance gastric feeding was done using oral gavage tubes inserted through the mouth into the stomach or lower esophagus to ensure administration of the compound into the stomach. Another batch of 5 female and 5 male served as control.

All experimental animals were observed for 15 days. Observations were made three times on the day of dosing and twice daily thereafter for the remainder of 14 days or until reversible toxic signs or symptoms subsided. All gross visible toxic signs and symptoms were recorded. Body weights were recorded prior to dosing and weekly thereafter.

In Swiss albino mice, weighing 25 grams, safe dose of 35 mg/mouse was observed for methylglyoxal while it was found to be 100 mg for methylglyoxal conjugates MGC-4, MGC-7 & MGC-8 and 75 mg MGC-2 and MGC-6 respectively. The results are summarized as shown below:

TABLE 12

Mortality In Swiss Albino Mice Orally Administered With Methylglyoxal And Its Conjugates

| Dosage level | Mortality | | | | | |
|---|---|---|---|---|---|---|
| | Methylglyoxal | MGC-2 | MGC-4 | MGC-6 | MGC-7 | MGC-8 |
| Control | 0/10 | 0/10 | 0/10 | 0/10 | 0/10 | 0/10 |
| 2.5X | 0/10 | 0/10 | 0/10 | 0/10 | 0/10 | 0/10 |
| 3.5X | 0/10 | 0/10 | 0/10 | 0/10 | 0/10 | 0/10 |
| 5X | 10/10 | 0/10 | 0/10 | 0/10 | 0/10 | 0/10 |
| 7.5X | 10/10 | 0/10 | 0/10 | 0/10 | 0/10 | 0/10 |
| 10X | 10/10 | 10/10 | 0/10 | 10/10 | 0/10 | 0/10 |

This clearly demonstrates that the conjugates of methylglyoxal are less toxic as compared to the parent molecule methylglyoxal and have a high therapeutic index, which is indicative of a better toxicity profile in humans.

What is claimed is:

1. A compound of formula (I)

wherein
$R_1$ is a $C_1$–$C_{12}$ straight or branched alkyl group, benzyl, or phenyl; And
$R_2$ is H or $COR_3$ where $R_3$ is a $C_1$–$C_6$ straight or branched alkyl group, benzyl or phenyl; or a pharmaceutically acceptable salt thereof.

2. A composition comprising the compound according to claim 1, or a pharmaceutically acceptable salt thereof and a pharmaceutically acceptable additive, carrier, diluent, solvent, filler, lubricant, excipient, binder or stabilizer.

3. The composition as claimed in claim 2, which provides 0.1 gram to 10.0 gram of the compound according to claim 1 or its pharmaceutically acceptable salt per unit dose.

4. The composition as claimed in claim 2, which provides 0.5 gram to 5.0 gram of the compound according to claim 1 or it pharmaceutically acceptable salt per unit dose.

5. The composition as claimed in claim 2, wherein the composition is a tablet, lozenge, capsule, powder, aqueous or oily suspension, syrup, elixir, implant or aqueous solution.

6. A method for treating cancer comprising administration of an effective amount of an imino acid conjugate of methylglyoxal of the formula (I):

where
$R_1$ is a $C_1$–$C_{12}$ straight or branched alkyl group, benzyl, or phenyl; and
$R_2$ is H or $COR_3$ where $R_3$ is a $C_1$–$C_6$ straight or branched alkyl group, benzyl or phenyl; or a pharmaceutically acceptable salt thereof to a patient in need thereof.

7. The method according to claim 6, wherein the cancer is cancer of the colon, prostate, larynx, kidney, pancreas, lung, breast, intestine, oral cavity, or ovary or glioblastorna or leukemia.

8. The method as claimed in claim 6, wherein the imino acid conjugate of methylglyoxal or the pharmaceutically acceptable salt of the imino acid conjugate, is administered to the patient in a pharmaceutically acceptable additive, carrier, diluent, solvent, filler, lubricant, excipient, binder or stabilizer.

9. The method as claimed in claim 6, wherein the imino acid conjugate of methylglyoxal, or the pharmaceutically acceptable salt of the imino acid conjugate, is administered in the form of a tablet, lozenge, capsule, powder, aqueous or oily suspension, syrup, elixir, implant or aqueous solution.

10. The method as claimed in claim 6, wherein a dose per day is 1 mg/Kg. B. Wt to 300 mg/Kg. B. Wt of the patient.

11. The method as claimed in claim 6, wherein a dosage is in the range of 10–100 mg/Kg. B. Wt of the patient.

12. A compound according to claim 1, which is selected from the group consisting of:

N-(1-hydroxy-2-ketopropyl)-methylpyroglutarnate;
N-(1-hydroxy-2-ketopropyl)-butylpyroglutamate;
N-(1-hydroxy-2-ketopropyl)benzylpyroglutamate;
N-(1-acetoxy-2-ketopropyl)-methylpyroglutamate;
N-(1-acetoxy-2-ketopropyl)-butylpyroglutamate;
N-(1-acetoxy-2-ketopropyl)-benzylpyroglutamate;
N-(1-hydroxy-2-ketopropyl)ethylpyroglutamate; and
N-(1-acetoxy-2-ketopropyl)-ethylpyroglutariiate; or
a pharmaceutically acceptable salt thereof.

13. A composition comprising the compound according to claim 12, or a pharmaceutically acceptable salt thereof and a pharmaceutically acceptable additive, carrier, diluent, solvent, filler, lubricant, excipient, binder or stabilizer.

14. The composition as claimed in claim 13, wherein the composition is a tablet, lozenge, capsule, powder, aqueous or oily suspension, syrup, elixir, implant or aqueous solution.

15. A method according to claim 6, wherein the imino acid conjugate of methylglyoxal of the formula (I) is selected from the group consisting of N-(1-hydroxy-2-ketopropyl)-methylpyroglutamate;
N-(1-hydroxy-2-ketopropyl)-butylpyroglutamate;
N-(1-hydroxy-2-ketopropyl)-benzylpyroglutamate;
N-(1-acetoxy-2-ketopropyl)-methylpyroglutamate;
N-(1-acetoxy-2-ketopropyl)-butylpyroglutamate;
N-(1-acetoxy-2-ketopropyl)-benzylpyroglutamate;
N-(1-hydroxy-2-ketopropyl)-ethylpyroglutamate; and
N-(1-acetoxy-2-ketopropyl)-ethylpyroglutamate; or
a pharmaceutically acceptable salt thereof.

* * * * *

UNITED STATES PATENT AND TRADEMARK OFFICE
CERTIFICATE OF CORRECTION

PATENT NO. : 6,613,793 B2
DATED : September 2, 2003
INVENTOR(S) : Anand C. Burman et al.

It is certified that error appears in the above-identified patent and that said Letters Patent is hereby corrected as shown below:

<u>Title page, Item [54] and Column 1, line 2,</u>
Title, "OR" should read -- OF --.

Signed and Sealed this

Twenty-third Day of December, 2003

JAMES E. ROGAN
*Director of the United States Patent and Trademark Office*